United States Patent
Nyholm

(10) Patent No.: US 7,804,933 B2
(45) Date of Patent: Sep. 28, 2010

(54) DENTAL COMPUTER TOMOGRAPHIC IMAGING

(75) Inventor: Kustaa Nyholm, Siuntio KK (FI)

(73) Assignee: Planmeca Oy, Helsinki (FI)

( * ) Notice: Subject to any disclaimer, the term of this patent is extended or adjusted under 35 U.S.C. 154(b) by 10 days.

(21) Appl. No.: 11/908,648

(22) PCT Filed: Mar. 13, 2006

(86) PCT No.: PCT/FI2006/050097

§ 371 (c)(1),
(2), (4) Date: Jul. 13, 2009

(87) PCT Pub. No.: WO2006/097576

PCT Pub. Date: Sep. 21, 2006

(65) Prior Publication Data

US 2009/0304148 A1  Dec. 10, 2009

(30) Foreign Application Priority Data

Mar. 14, 2005  (FI) .................................. 20050271

(51) Int. Cl.
*A61B 6/14* (2006.01)
(52) U.S. Cl. ........................................................ 378/39
(58) Field of Classification Search .................. 378/4, 378/19, 20, 38, 39
See application file for complete search history.

(56) References Cited

U.S. PATENT DOCUMENTS

| 6,118,842 | A | 9/2000 | Arai et al. |
| 6,452,997 | B1 | 9/2002 | Muller et al. |
| 6,466,641 | B1 * | 10/2002 | Virta et al. ................. 378/38 |
| 2001/0036246 | A1 | 11/2001 | Graumann |
| 2003/0235265 | A1 | 12/2003 | Clinthorne et al. |
| 2004/0008820 | A1 | 1/2004 | Schmitt |

FOREIGN PATENT DOCUMENTS

| EP | 1 457 155 A1 | 9/2004 |
| EP | 1 491 145 A1 | 12/2004 |
| WO | 03/010556 | 2/2003 |

\* cited by examiner

*Primary Examiner*—Irakli Kiknadze
(74) *Attorney, Agent, or Firm*—Cozen O'Connor

(57) ABSTRACT

This invention directed to a computer tomography imaging apparatus designed for dental use as well as to methods realizable by it, especially to a method for relative positioning of the imaging means and the patient for imaging. A relevant feature of the computer tomography imaging device according to the invention is an arm construction consisting of turnable arm parts. The use of the construction enables implementation of, particularly, a so-called Cone Beam computer tomography apparatus (CBCT) as lighter, and more inexpensive realization of it, than has been the case regarding CT devices of prior art, especially when thinking of their use in odontology.

14 Claims, 2 Drawing Sheets

DENTAL COMPUTER TOMOGRAPHIC IMAGING

Figure 1:
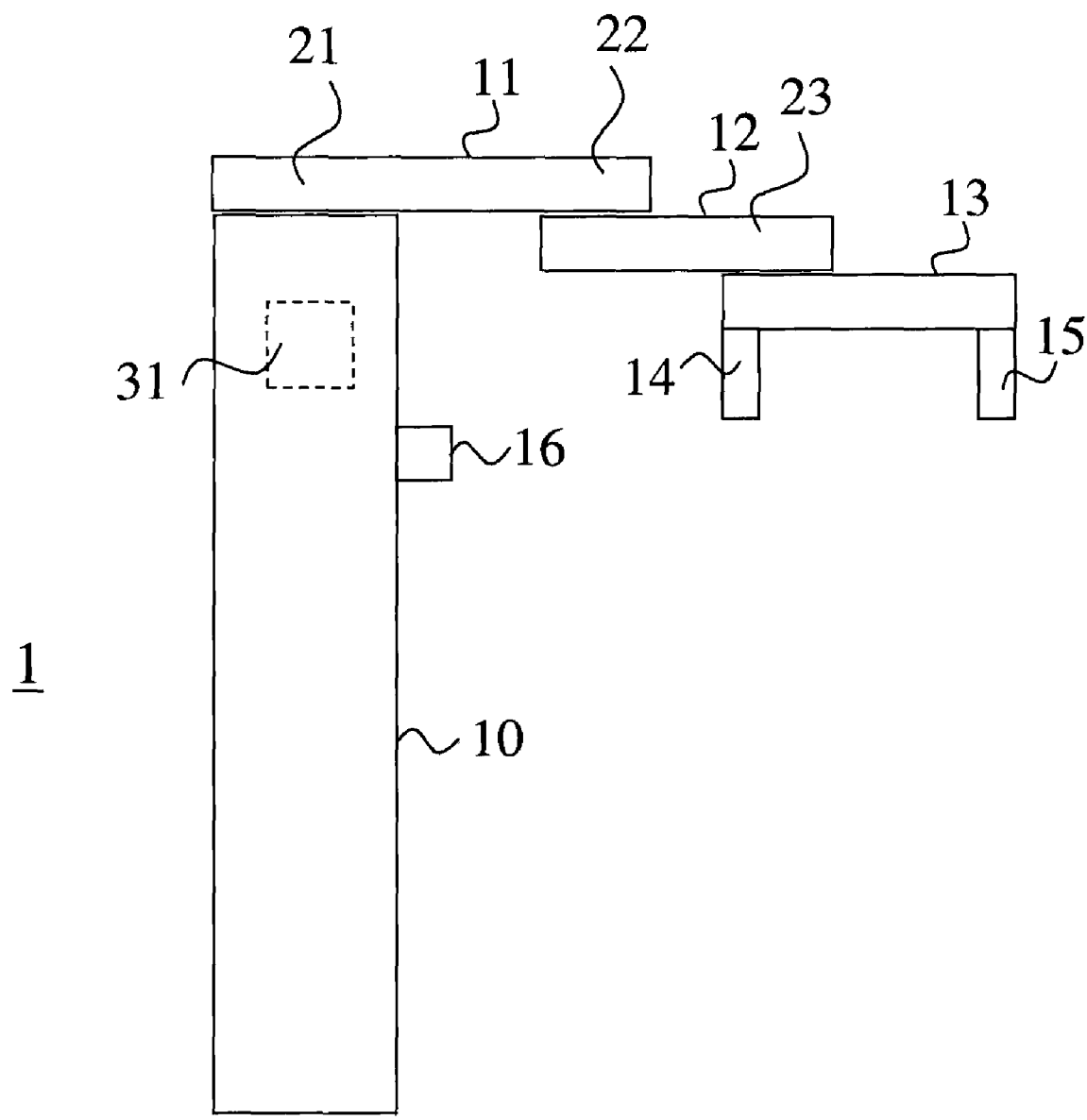

This invention relates to a computer tomography apparatus designed for dental use and methods to be realised by it, especially to a method for positioning imaging means and the patient with respect to each other for imaging.

Medical X-ray imaging has a long history. The earliest techniques were based on transillumination of the object to be imaged. In transillumination, all the anatomies of the volume being imaged possibly overlapping in the direction of radiation are imaged on the film on top of each other. In order to solve this problem, layer i.e. so-called tomographic imaging was later developed, by means of which it is possible to get the desired layer of the object to become imaged more clearly by causing blurring of the other layers of the object in the image to be formed. Blurring is accomplished by changing relative position of the imaging means and the object during an imaging event, depending on the imaging procedure, either during irradiation or between individual irradiations.

Later on, and especially along with the advancement of computers and digital imaging, a great number of different tomographic imaging techniques and devices have been developed. In the field of odontology one generally uses, in addition to intra-oral and cephalometric imaging, which are simpler as far as imaging technology is concerned and are realised by transillumination imaging, among other things, so-called panoramic imaging in which, typically, a layer comprising the whole dental arch is imaged on a plane. In conventional film-based panoramic imaging one scans over the dental arch with a narrow beam so that the centre of rotation of a turnable arm part, substantially to the opposite ends of which the imaging means have been positioned, is transferred linearly while the arm part is turned and at the same time a film, which is moving together with the arm part, is transferred through a narrow beam produced by the radiation source in a rate fulfilling the imaging condition of the imaging procedure in question. In digital panoramic imaging, the frequency by which the image data is read from the sensor during an imaging scan corresponds this transfer velocity of the film.

Lately, an interest has begun to arise to apply computer (or computed) tomography (CT), used earlier mainly in hospital environment, also in the field of odontology. As such, one is not able to transfer these massive and expensive CT apparatuses of hospital use to the dental environment, on account of their size but especially also on account of their price.

Imaging-technically, several different CT technologies are known today. In CT imaging, the volume to be imaged is irradiated from different directions and, from the data thus acquired, a desired two- or three-dimensional image is reconstructed afterwards. By this kind of technology one is also able, in principle, to reconstruct, among other things, a two-dimensional image outspread on a plane of a part of dental arch or, if you like, of the whole dental arch. A panoramic image having been reconstructed in this way is not, however, identical with such a (digital) panoramic image having been taken by conventional methods, wherein imaging of the desired layer is based on blurring of the non-desired layers. As far as principles of computer tomography and its different applications are concerned, a reference can be made to the literature on the art, such as to *Computed Tomography: Principles, Design, Artifacts and Recent Advantages*, Jian Hsich, SPIE PRESS, 2003, Bellingham, Wash., USA.

Medical computer tomography apparatuses conventionally comprise a horizontal plane on which the patient is positioned for the duration of imaging. Such devices are quite massive and expensive when comparing them e.g. to dental panoramic, or combined panoramic/cephalometric imaging devices. The great size and weight of CT devices has been a consequence of different limiting conditions of the imaging technology, such as the radiation intensity required. Because of the massive structure, one has tried to realise the relative movements of the imaging means and the object so that the imaging means themselves are arranged either stationary or to be turnable with respect to a stationary centre of rotation only, whereby the other possible movements may be realized by arranging the object to be imaged itself as movable.

A form of computer tomography is the so-called cone beam CT (CBCT) in which one uses, as a distinction from the narrow beam used in e.g. panoramic imaging, a cone-like beam substantially the size of the dimensions of the volume to be imaged and, instead of a slot sensor, a detector the size of which corresponds the size of the beam in question. Compared to many more conventional CT imaging technologies, with the CBCT technology, one is able to reach significantly smaller radiation doses and shorter imaging times.

Lately, one has begun developing CT apparatuses intended especially for dental imaging. A typical starting point also in these solutions as outlined and realised has been arranging the imaging means to a relatively massive, stabile support construction. Thus, the prior art includes, among other things, CT devices in which the patient is positioned in a sitting position on a chair in between the imaging means, and the possible relative movements of the patient position and the imaging means, for positioning the imaging means ready for imaging of a desired volume, are realised by moving the chair.

One CT device according to prior art has been presented in WO publication 03/84407. The body of the device in question forms a stabile gate-like structure under which a chair is arranged, into which the patient is positioned for the duration of imaging, as immovable as possible. The imaging means are arranged turnable on a plane around a centre of rotation, which is fixedly located with respect to the body part of the device. The patient chair is arranged movable in the x, y, z coordinate system, whereby the location of the centre of rotation of the imaging means and the height position of the imaging means with respect to the anatomy of the patient can be changed, if desired.

On the other hand, e.g. in the U.S. Pat. No. 6,118,842 a structure has been outlined, which would enable both turning the imaging means with respect to the centre of rotation and changing their position by means of a moving mechanism of the arm part comprising the imaging means. It is presented that in the solution according to the publication a detector size of e.g. 5×5 cm is to be used. The dimensions of the apparatus and the detector enable gathering information for reconstructing a volume of some portion of a skull by turning the imaging means with respect to a centre of rotation. If one desires to get larger, more or e.g. adjacent volumes reconstructed by the apparatus, one has to repeat the imaging and between each imaging arrange anew the relative position of the object and the imaging means to be as desired.

The object of the present invention and its preferable embodiments is to provide a CT apparatus comprising a novel arm structure. Additionally, an object of the invention is to provide a new kind of method for relative positioning of especially the patient and the imaging means for computer tomography imaging. Especially, an object is to provide such a CT apparatus for especially dental imaging, which may be realised significantly more inexpensively than conventional medical CT apparatuses. The aim is to implement the invention in such a way that the patient can be positioned immovable to the body of the apparatus, or to some other stationary patient station, on the horizontal plane at least, and to realise the movements needed to change the relative position of the patient and the imaging means by moving the imaging means. The invention together with its preferable embodiments enable realising the arms structure of the CT apparatus as a construction, which one is able to arrange as relatively light but still stabile enough and which enables, as a starting point, an easier way to position the patient with respect to the imaging means when compared to moving the patient.

Essential features of the invention are presented in the enclosed claims. Thus, it is essential for the CT apparatus according to the invention that it comprises an arm structure by which the position of the arm part included to the arm structure and comprising the imaging means may be changed with respect to the patient support means of the apparatus, which arm part comprising the imaging means is connected to a body part of the apparatus or to some other structure which is fixed with respect to the patient support means via at least two other turnable arm parts, which each of the at least two arm parts is arranged to be turnable with respect to at least two centres of rotation located at a distance from each other substantially on the same plane, out of which centres of rotation the outmost centres of rotation of the outmost arm parts of said at least two arm parts connect, on the one hand, to the arm part comprising imaging means and, on the other hand, to the body part or other structure which is fixed with respect to the patient support means. Applying such an arms structure in a CT apparatus enables realising patient positioning without moving the patient by transferring the arm part comprising the imaging means to a desired position for imaging with respect to the patient.

The imaging means of the CT apparatus according to the invention include especially and preferably an area sensor, a so-called frame sensor, used in CBCT imaging. The active surface of the sensor may be circular or a rectangle the dimensions of which preferably being substantially of the same order of magnitude, such as e.g. at least 10×10 cm, such as 12×12 cm, or e.g. 20×20 cm, or a sensor of corresponding diameter. By arranging collimation of the beam produced by the radiation source to correspond the dimensions of such a sensor, and by using a source-image-distance (SID) of e.g. the order of 50 cm, the radiation source of the apparatus according to the invention may be realized as considerably lighter than those of the conventional computer tomography apparatus. Thus, also the arm structure may be realised as relatively light, whereby it is relatively simple to realise it as a structure according to the invention enabling moving the location of the rotation arm. In this way, positioning is enabled which may be realised in a simpler way than by moving the patient, which, among other things, facilitates moving from one imaging position of a partial volume to another.

Figure 2:
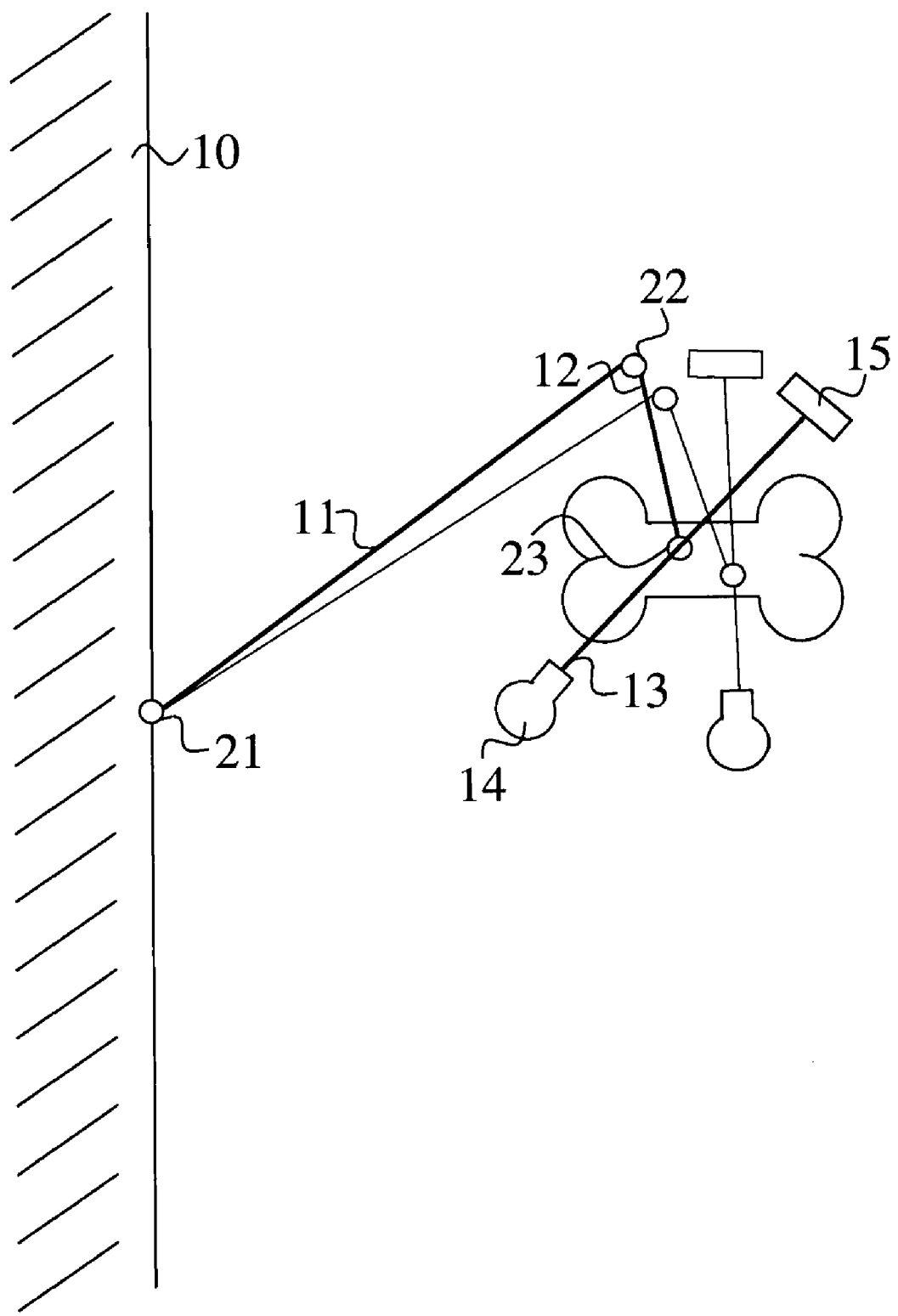

The invention, its preferable embodiments and their objects and benefits are described more closely in the following by referring also to the enclosed figures, of which FIG. 1 shows as simplified one CT apparatus according to the invention and FIG. 2 illustrates how imaging means may be transferred according to the invention, with the help of the arms structure of the apparatus according to FIG. 1, to a new imaging position with respect to the object.

FIG. 1 shows as simplified one CT apparatus 1 according to the invention. The basic structure of the apparatus consists of a body part 10 and of three arm parts 11, 12, 13 being connected to it. The first arm part 11 is arranged to be turnable around a centre of rotation 21 with respect to the body part 10 and around a centre of rotation 22 with respect to the second arm part 12, whereby the second arm part 12 is thus turnable around a centre of rotation 22 with respect to the first arm part 11 and, additionally, is arranged to be turnable around a centre of rotation 23 with respect to the arm part 13, which comprises imaging means (a radiation source 14 and a detector 15), whereby the arm part comprising imaging means 14, 15 is thus turnable around a centre of rotation 23 with respect to said second arm part. The apparatus additionally includes patient support means 16 arranged in connection to the imaging station, the support means being arranged to the body part 11 in a solution according to FIG. 1. The first arm part 11 may also be attached e.g. to a ceiling or a wall, whereby the apparatus according to the invention does not necessarily include an actual body part 10 at all and whereby the patient support means 16 are arranged to some other fixed location with respect to the centre of rotation 21 of the first arm part 11 than to the body part 10.

It is also possible to realise the invention, according to an embodiment not shown in FIG. 1, so that vertical freedom of movement is arranged to the arm structure 11, 12, 13 of the apparatus, too. In an apparatus having a vertical body part 10 this can be realised, among other things, in such a way that the patient support means 16 is brought to move along with the vertical movement of the arm structure 11, 12, 13, or by arranging independent vertical freedoms of movement to both of them. In this case, it is possible to position the location of the volume to be imaged without moving the patient also in vertical direction.

The apparatus according to the invention additionally includes operating devices not shown in FIG. 1 and a control system for turning said arm parts in a desired way/to a desired position. Additionally, the apparatus includes control systems, schematically shown at 31, and routines needed for controlling, among other things, functions of the detector and the radiation source and movements of the arm parts.

There has not necessarily been arranged means needed for processing the information detected by the detector 15 in the CT apparatus according to the invention as such, in which case the apparatus is arranged in connection with a separate computer. The detector used in the apparatus may be e.g. a CMOS or a detector based on so-called direct detection. One is able to reconstruct an image of the information detected by the detector by methods known as such, such as so-called cone beam or iterative algorithms.

An especially preferable and essential embodiment of the invention comprises then an area detector as an imaging detector. Active surface of the detector may be realised as essentially circular, but preferably essentially as a square, i.e. as a detector the width and height of which being of the same order of magnitude. The dimensions of such a detector are essentially at least of the order of centimeters, such as e.g. at least 10×10 cm, or 12×12 cm, or e.g. 20×20 cm. By arranging collimation of the beam produced by the radiation source corresponding to the size of such a detector, and by using SID of the order of e.g. 50 cm, it is possible to realize radiation source of the apparatus according to the invention as remarkably lighter than in the conventional computer tomography devices. This is possible as a consequence of that, it would be possible to arrange imaging time in such a construction to be so short that, in connection with dental imaging, it may even be prolonged to some extend from this theoretical minimum, whereby one is able to use a lower power and thus a lighter x-ray source. Thus, also the arm structure may be realised relatively light, whereby the structure is relatively simply realisable as a structure according to the invention enabling moving the position of the imaging means. By this, positioning of the imaging means is enabled which is simpler to realise than moving of the patient, which, among other things, facilitates moving from one imaging position of a partial volume to another.

In the control system of the apparatus, control routines have preferably been arranged for enabling, on the one hand, pulsed function of the radiation source and, on the other hand, periodical saving and/or forwarding of the information detected by the imaging detector. Preferably, the information of the detector has been arranged to be read several times per second, such as e.g. over 10 times per second. Periodizing of the irradiation is preferably synchronized with the function of the detector in such a way that irradiation is always cut off while information is being read out from the detector. Preferably, the frequency is arranged to be of such order at least that duration of the radiation pulse corresponds with the maximum distance corresponding the intended reconstruction voxel size—or, that is, the duration of the radiation pulse has been arranged to be shorter than the time it may take for the beam, as maximum, to turn in a volume to be imaged a distance corresponding the intended reconstruction voxel size. One may also arrange duration of the radiation pulses to be shorter, even essentially shorter than the time it takes for the imaging detector to move during imaging a distance corresponding to the detector pixel size. The pixel size of the imaging detector may be arranged to be of the order of 200 µm, but along with development of technology even smaller. The imaging detector is arranged in functional connection with a computer, which computer comprises means for reconstructing a two- or a three-dimensional image of the information detected by the detector.

FIG. 2 illustrates positioning of the centre of rotation 23 of the arm part 13 comprising imaging means 14, 15 at two different points with respect to the object to be imaged. Coordinates of the desired centres of rotation may be input to the control system of the apparatus via a user interface, or positioning lights known as such or another corresponding arrangement may be arranged to the apparatus, from which the coordinates of the desired point may be arranged to be transmitted automatically to the control system. Control system may also include one or more pre-given positions of the imaging means 14, 15, as well as control routines, by means of which several individual volumes can be imaged automatically one after another—such as at least two such positions arranged to be located at such a distance from each other that a joint image may be reconstructed of the information produced during the imagings in question. In that case, the control routine may comprise not only control commands to transfer, in a functional range of the arm structure 11, 12, 13, the centre of rotation 23 of said turnable arm part 13 comprising the imaging means 14, 15 to a predetermined (or to one input in the control system) coordinate point of initiation of imaging, and to realise imaging with respect to these points, but also control commands for positioning said turnable arm part 13 comprising imaging means 14, 15 at a predetermined angle with respect to said imaging point, when positioning said centre of rotation 23 of the arm part 13 including the imaging means to the coordinate point of initiation of imaging. One such a ready-made control routine may comprise driving of the imaging means and imaging with respect to at least two such points of initiation of imaging, the distance of which being such that of the information produced at the locations in question, one is able to reconstruct a joint image. Such a control routine may comprise e.g. imaging of three different partial volumes at such centres of rotation with respect to the patient support means that, of information received, an image of the whole dental arch may be reconstructed by stitching the reconstructed images to a one whole image by making use of algorithms known as such.

It is well known by those skilled in the art that, especially with advancing technology, the basic idea of the invention may be realised in many different ways and its different embodiments are not limited to the examples described above but they may vary within the scope defined by the accompanied claims.

The invention claimed is:

1. A dental computer tomography apparatus, which includes:
   an arm structure connected to a body part (10) of the apparatus (1) or to a fixed structure not belonging to the actual apparatus (1),
   which arm structure includes an arm part (13) comprising imaging means (14, 15) and which is turnable around a centre of rotation (23),
   which said imaging means comprise a radiation source (14) and an imaging detector (15), which are located essentially at the opposite ends of said arm part (13),
   a collimator structure for limiting radiation produced by the said radiation source (14) to a beam,
   patient support means (16) in connection with an imaging station arranged in connection with the apparatus, and
   a control system (31) for controlling and realizing operation and movements of said radiation source (14) and imaging detector (15), as well as for controlling and realizing movements of said arm structure,
   wherein said arm part (13) comprising the imaging means (14, 15) is connected to said body part (10) of the apparatus, or to some other structure of the apparatus which is fixed with respect to the patient support means (16), via at least two other turnable arm parts (11, 12), which each of the at least two arm parts (11, 12) is arranged to be turnable with respect to at least two centres of rotation (21, 22, 23) locating at a distance from each other substantially on the same plane, out of which centres of rotation (21, 22, 23), the outmost centres of rotation (21, 23) of the outmost arm parts (11, 12) of said at least two arm parts connect, on the one hand, to said arm part (13) comprising imaging means and, on the other hand, to said body part (10) or other structure which is fixed with respect to the patient support means (16).

2. The apparatus according to claim 1, wherein said control system (31) comprises a control routine, which includes control commands to transfer, in a functional range of the arm structure (11, 12, 13), the centre of rotation (23) of said turnable arm part (13) comprising imaging means (14, 15) to a predetermined coordinate point of initiation of imaging, or to such coordinate point input in the control system.

3. The apparatus according to claim 1, wherein the said control system (31) comprises a control routine, which includes control commands for positioning said turnable arm part (13) comprising imaging means (14, 15) at a predetermined angle with respect to said imaging station, when positioning said centre of rotation (23) of the arm part (13) comprising imaging means (14, 15) to a coordinate point of beginning of imaging.

4. The apparatus according to claim 1, wherein said control system (31) comprises a control routine, which includes control commands for driving said arm structure (11, 12, 13) so, that the arm part (13) included therein and comprising imaging means (14, 15) turns during the imaging with respect to the centre of rotation (23) to produce information about the volume in question of the object to be imaged.

5. The apparatus according to claim 1, wherein said control system comprises a control routine, which includes control commands for driving said arm structure (11, 12, 13) to at least two predetermined starting positions of the imaging in which the centre of rotation (23) of the turnable arm part (13) comprising imaging means (14, 15) is located in a predetermined coordinate point, and control commands for realizing imaging in the positions in question to produce information concerning at least two volumes of the object.

6. The apparatus according to claim 5, wherein said at least two imaging positions are arranged to be located in such a distance from each other, that a joint image can be reconstructed of the information produced during the imagings in question.

7. The apparatus according to claim 6, wherein said control system comprises a control routine, which includes control commands for driving said arm structure (11, 12, 13) to three predetermined starting positions with respect to a dental arch to be imaged and for realizing imaging in said imaging positions in such a way that a joint image comprising the whole dental arch may be reconstructed from the information produced during the imaging.

8. The apparatus according to claim 1, wherein said imaging means (14, 15) are arranged to said arm part (13) comprising imaging means at a distance of the order of 50 cm from each other.

9. The apparatus according to claim 1, wherein said imaging detector (15) is an area detector, i.e. a detector which is circular, or the width and height of which are of the same order of magnitude, the dimensions of which detector being at least of the order of centimeters, such as an area detector of the size of e.g. at least 10×10 cm, such as 12×12 cm, or 20×20 cm, to which is connected, together with the control system of the apparatus, means for periodically detecting and storing or forwarding the information received by the detector.

10. The apparatus according to claim 9, wherein said imaging detector (15) is arranged to store and/or forward the information it has received several times per second, such as e.g. over 10 times per second.

11. The apparatus according to claim 9, wherein the pixel size of the imaging detector (15) is of the order of 200 µm.

12. The apparatus according to claim 1, wherein said control system is arranged to control said radiation source (14) to produce radiation as pulsed and to control reading of the information from said imaging detector (15) to take place at those times of the pulse in question when irradiation is cut off.

13. The apparatus according to claim 12, wherein duration of one radiation pulse is arranged to be shorter than the time that it may take for the beam, at the maximum, to turn in the volume to be imaged a distance corresponding the intended reconstruction voxel size, or to be shorter or essentially shorter than the time it takes for said imaging detector (15) to move during imaging a distance corresponding the length of one detector pixel.

14. The apparatus according to claim 1, wherein said imaging detector (15) is arranged in functional connection with a computer, which computer comprises means for reconstructing a two or a three-dimensional image of the information detected by the detector (15).

* * * * *